United States Patent [19]

Bifulk

[11] Patent Number: 5,340,310
[45] Date of Patent: Aug. 23, 1994

[54] DENTAL PROPHY ANGLE

[76] Inventor: Edward J. Bifulk, 1948 E. Kenwood Dr., St. Paul, Minn. 55117

[21] Appl. No.: 134,397

[22] Filed: Oct. 12, 1993

[51] Int. Cl.$^5$ .................................................. A61C 3/03
[52] U.S. Cl. ..................................... 433/123; 433/122; 433/125; 433/126
[58] Field of Search ............... 433/118, 122, 123, 124, 433/125, 130, 126, 133

[56] References Cited

U.S. PATENT DOCUMENTS

| | | | |
|---|---|---|---|
| 2,093,682 | 9/1937 | Levy | 433/124 |
| 3,073,031 | 1/1963 | Brenman et al. | 433/122 |
| 4,834,653 | 5/1989 | Edwardson | 433/118 |

Primary Examiner—Cary E. O'Connor
Attorney, Agent, or Firm—Clayton R. Johnson

[57] ABSTRACT

A disposable attachment for reciprocably mounting a dental tool and being mounted to a conventional handpiece which provides the drive for the tool. The attachment includes a plastic housing having a neck and sleeve to rotatably mount a shaft which is driven by a dental handpiece and a head which mounts a plastic socket to be reciprocated by a shaft eccentric extended into an annular groove in the socket. A rotational restrainer is provided in the socket groove to permit rotation of the tool which is friction fitted in the socket while a force external to the attachment is exerted on the tool but otherwise retain the tool in a fixed angular relationship relative to the head as the socket is reciprocated. The attachment housing, socket and rotational restrainer are made of plastic while in one embodiment the attachment shaft is also made of plastic.

12 Claims, 7 Drawing Sheets

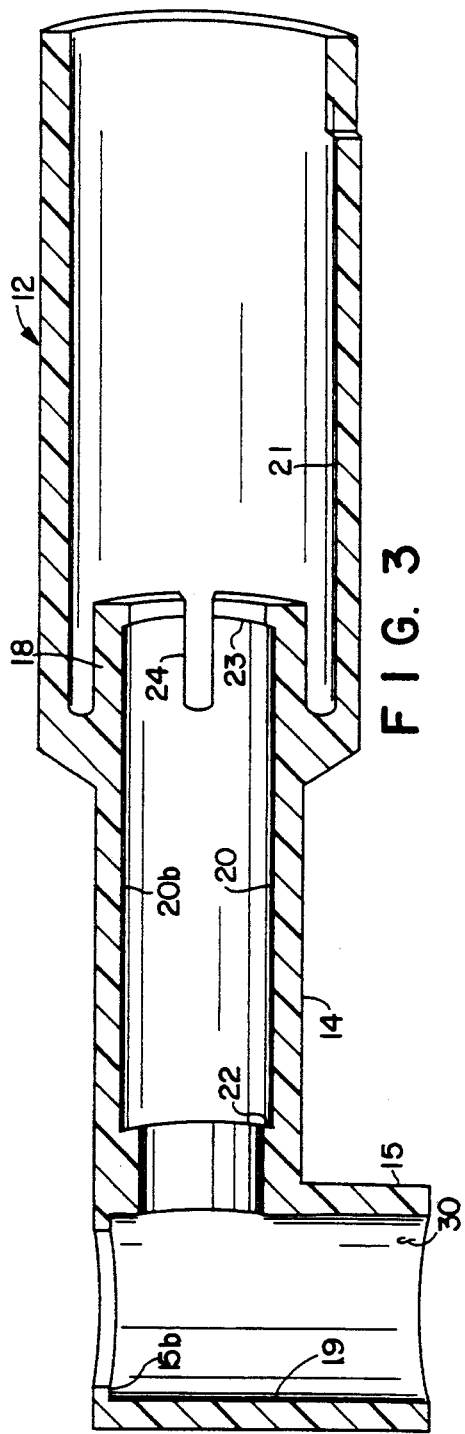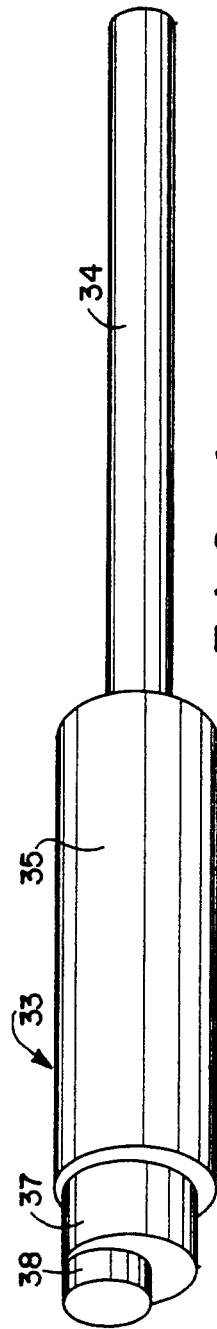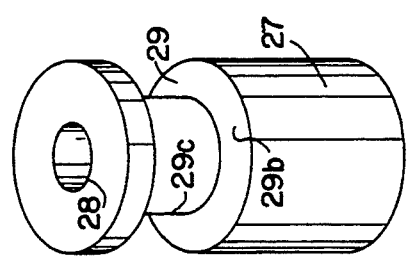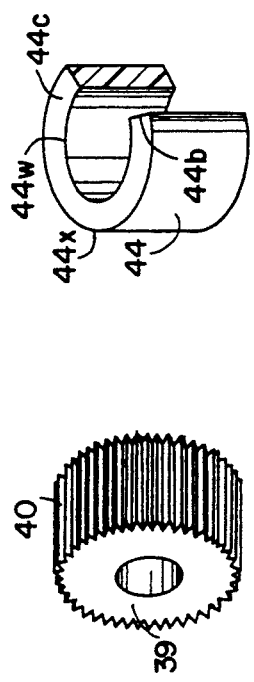

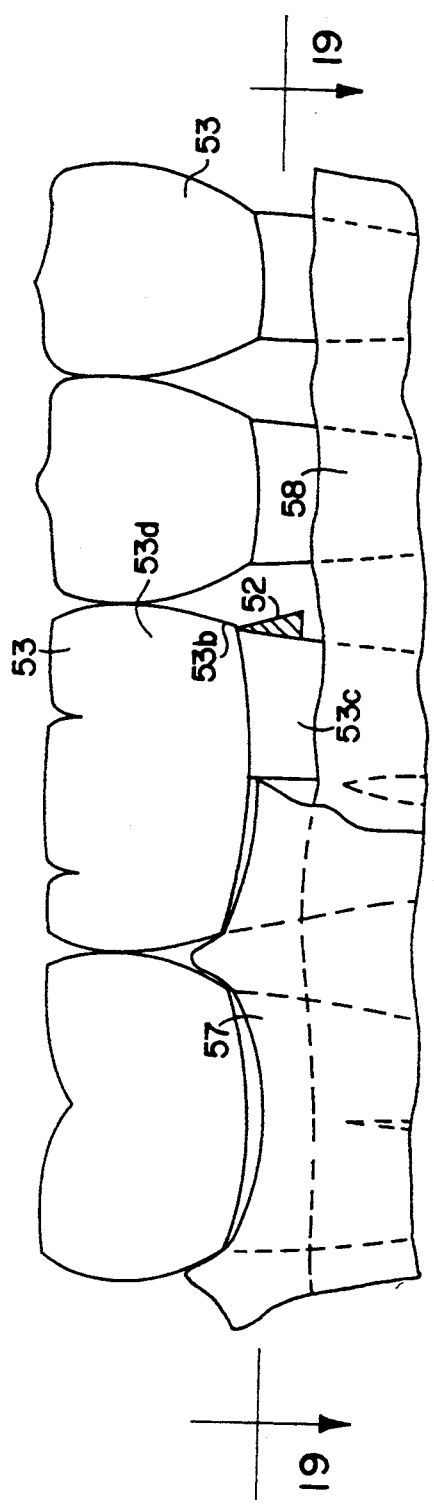
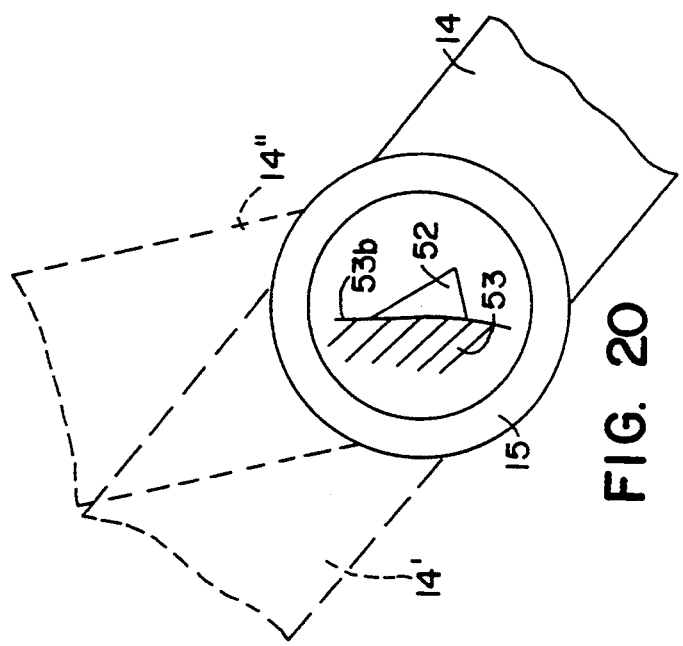
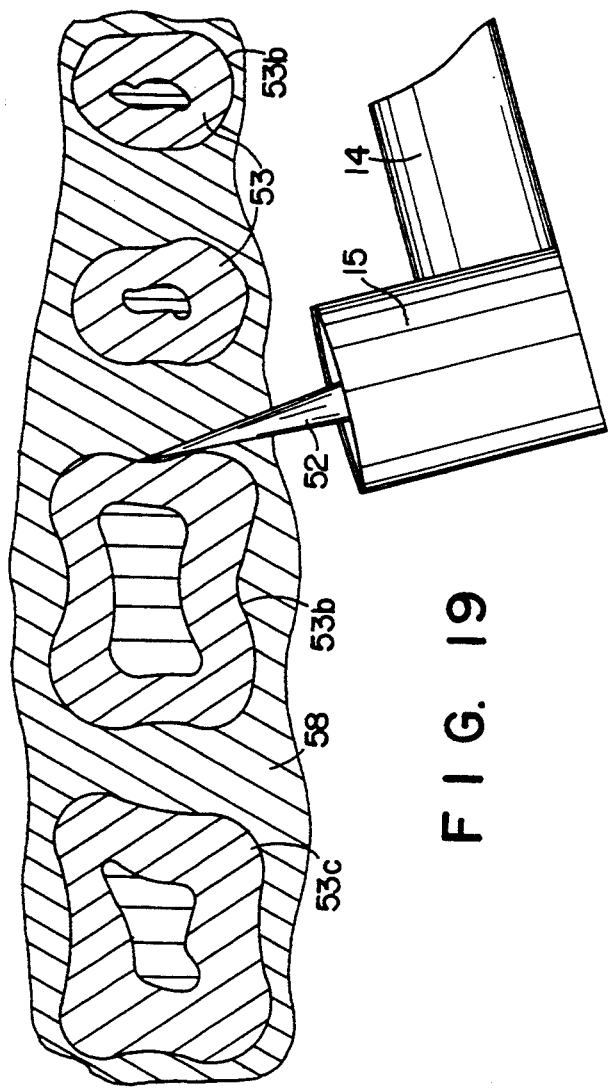

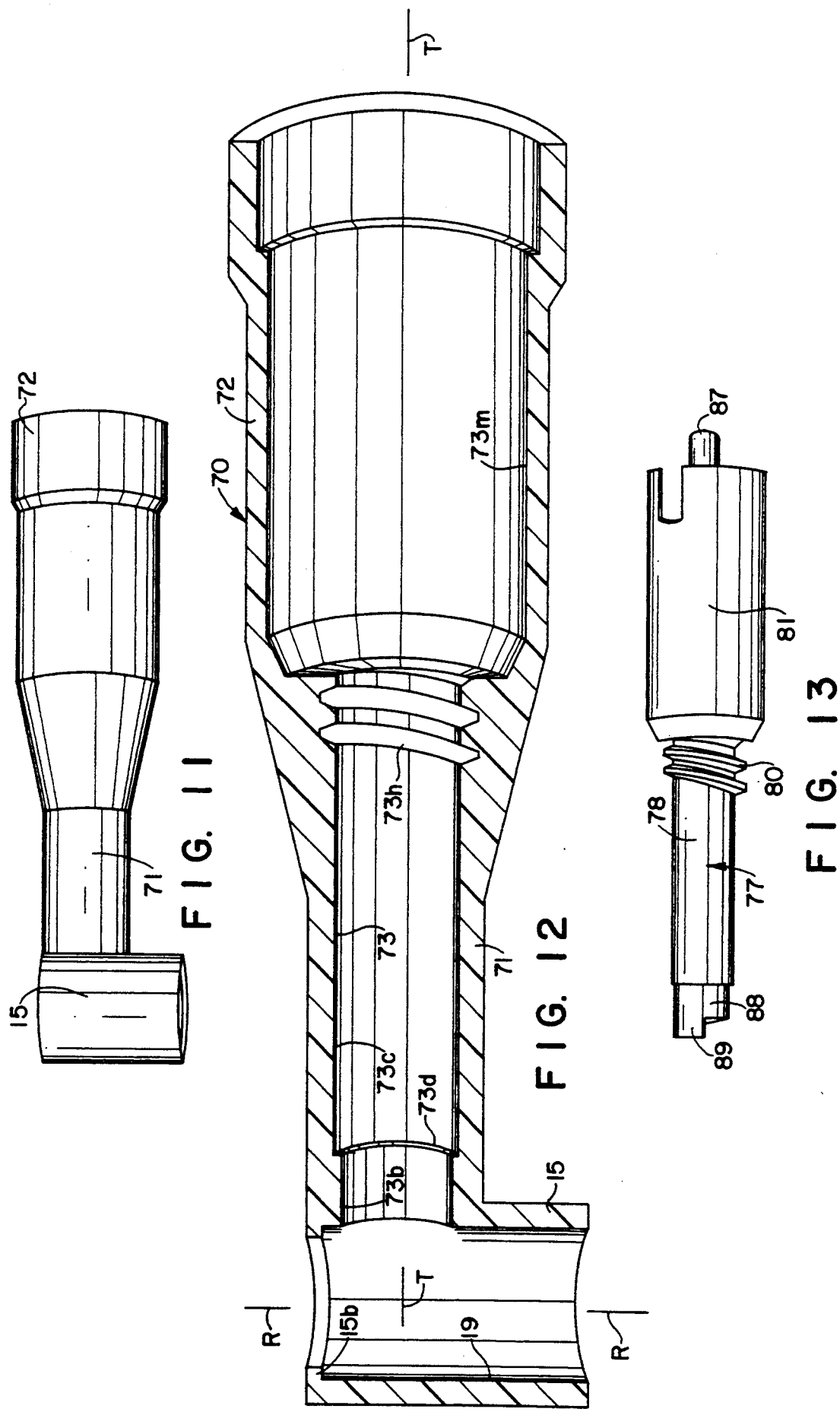

DENTAL PROPHY ANGLE

BACKGROUND OF THE INVENTION

This invention relates to disposable dental apparatus that is particularly adapted for cleaning and carrying out other treatments of the surfaces of the interproximal human teeth.

Rotary tools such as rubber cups or brushes have been used for removing pellicle, plaque and accretions from teeth. Such rotary tools are very good for removing such material from buccal and lingual surfaces of teeth but only reach part way into the interproximal surfaces of the teeth. It is known in the prior art to provide dental apparatus for reciprocating dental tools for cleaning, polishing, removing plaque and carrying out other types of treatment of teeth, for example see U.S. Pat. Nos. 5,040,977, 4,976,625 and 4,954,082 to Weissman; 3,552,022 to Axelsson; and 4,526,541 to Hubschmid. U.S. Pat. No. 4,834,653 to Edwardson discloses dental apparatus for vibrating a dental tool. In order to provide improved apparatus for carrying out various dental operations on teeth, particularly for removing material from interproximal surfaces of teeth, and such apparatus is of a disposable type, this invention has been made.

SUMMARY OF THE INVENTION

A disposable prophy angle attachment is adapted to be driven by a conventional handpiece for reciprocating a dental tool, the attachment including a plastic housing for rotatingly mounting a shaft and a plastic annular socket reciprocally mounted in the housing head. The shank of the tool forms a friction fit with the wall defining the socket bore and remains in the socket bore, even as the tool is reciprocated, until manually removed. The attachment shaft has an eccentric pin extended into an annular groove in the socket for reciprocating the socket while a plastic rotational restrainer is provided in the socket groove to prevent rotation of the socket and the tool relative to the head when no external resistance is encountered by, or no pressure is applied to, the tooth engaging portion of the tool, but to permit rotation of the socket so that the tool is self adjusting upon encountering a tooth or gum surface for carrying out a dental treatment procedure. In one embodiment, the shaft is made of disposable plastic while in a second embodiment, a second plastic housing is provided in the first mentioned housing to rotatably mount the attachment shaft, which may be made of metal.

One of the objects of the invention is to provide a new and novel dental attachment for reciprocating a dental tool. A further object of this invention is to provide new and novel means for reciprocating a dental tool while retaining the tool in a substantially fixed angular relationship to the attachment head when the tooth engaging portion of the tool is not exposed to an external resistance, and to permit rotation of the tool to self adjust for proper orientation to perform a dental operation on a tooth so as to minimize possible injury to the gums and undesired removal of material from hard tissue such as a tooth.

For convenience, "longitudinal" refers to the general direction that a dental tool is reciprocated in the housing head of the attachment, "transverse" refers to the general direction that the housing neck extends away from the housing head, and "external resistance" refers to the resistance to movement of the tool resulting from the tool encountering a surface other than a part of the dental attachment.

BRIEF DESCRIPTION OF THE DRAWINGS

FIG. 3 is a cross sectional view, somewhat in perspective, of the housing of the first embodiment;

FIG. 4 is a perspective view of the drive member of the first embodiment;

FIG. 5 is a perspective view of the bushing of the first embodiment;

FIG. 6 is a perspective view of the socket of the first embodiment;

FIG. 7 is a partial perspective view of the rotational restrainer of the first embodiment;

FIG. 8 is a somewhat diagrammatic view showing of a plurality of teeth together with the adjacent part of the gingiva extending above the bone structure and part of the gingiva broken away to show the bone structure adjacent to the teeth in a solid line, said view also diagrammatically showing the tooth engaging portion of the tool in cross section as it is being utilized to treat a tooth;

FIG. 11 is primarily a side view of the outer housing of the second embodiment;

FIG. 12 is a cross sectional view, partly in perspective, of the outer housing of the second embodiment;

FIG. 13 is a perspective view of the attachment inner housing of the second embodiment together with the drive member of the second embodiment rotatably mounted therein;

FIG. 19 is a cross sectional view generally taken along the line and in the direction of the arrows 19—19 of FIG. 8 to show a portion of the prophy angle and the roots of the teeth with the bone and gum tissue broken away; and FIG. 20 is a bottom view of the front end portion of the attachment and tool of the first embodiment; said view showing the attachment in one angular position in solid lines and two additional angular positions in dotted lines to illustrate different angles that the prophy angle may be rotated to when the tool engages a tooth surface which is diagrammatically illustrated.

Figure 1:
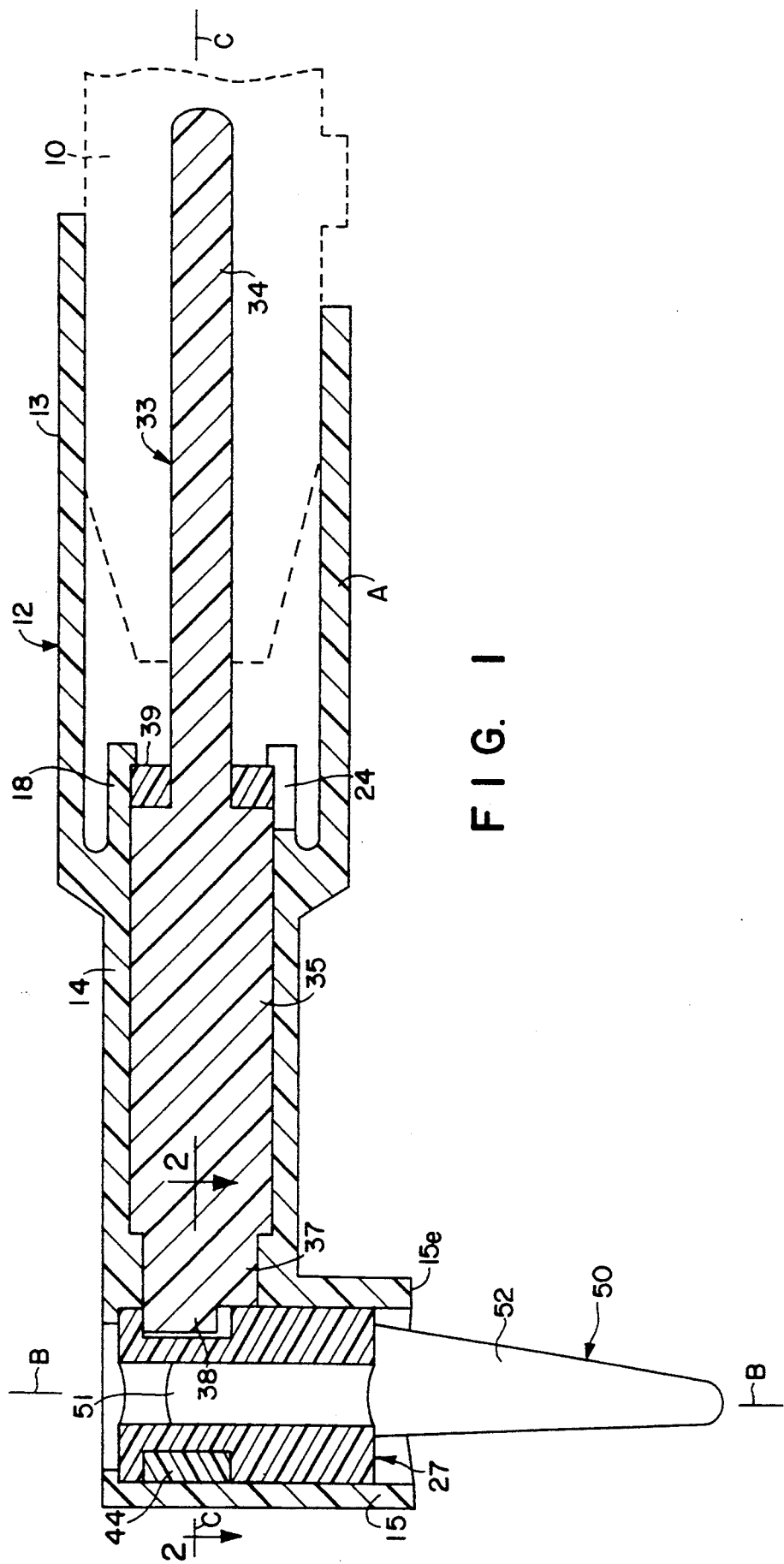
FIG. 1 is a cross sectional view of the dental handpiece attachment of the first embodiment of the invention mounting a dental tool to be reciprocated thereby and showing a portion of a conventional dental handpiece in phantom.

Referring in particular to FIGS. 1-7, the disposable attachment A of the first embodiment includes a housing, generally designated 12, having a transversely extending sleeve 13 which at one axial end portion is adapted for being mounted to a conventional handpiece 10, a transversely elongated neck 14 having one end joined to the axial opposite end of the sleeve, and a longitudinally extending head 15 that is joined to the axial opposite end of the neck. Advantageously, the outer diameter of the neck is substantially smaller at its juncture to the head than the outer diameter at the juncture of the sleeve to the neck. The head has a generally longitudinal cylindrical bore 19 extending axially therethrough at a generally right angle to the direction of extension of the neck away from the head, including opening through the lower terminal annular edge (surface) 15c of the head.

The neck has a bore 20 extending transversely therethrough to, advantageously, have its central axis extend at substantially right angles to the central axis B—B of the head bore 19 and open to the head bore. Further, the sleeve has a bore 21 of a larger diameter than the diameter of the neck bore and advantageously extends transversely coaxially therewith, the sleeve and neck having a central axis C—C. An axially slotted collar 18 is joined to the neck to extend coaxially within the sleeve and provide an annular clearance space therebetween, the collar having circumferentially spaced slots 24 that extend axially to open through the shoulder 23 toward the free terminal end of the collar.

A circular cylindrical socket 27 is mounted in the head bore for reciprocal movement in longitudinal directions, and rotary movement about the axis B—B relative to the head, the bore 19 having a reduced diameter portion to form an annular flange 15b to limit axial movement of the socket in a longitudinal direction away from the head terminal annular surface 15c. The socket has one or more protrusions 30 extending into the head bore axially remote from the shoulder 15b to, in conjunction with the shoulder 15b, retain the socket in the head bore prior to the mechanism for reciprocating the socket being mounted in its driving position by the housing. The protrusions are of sufficient resiliency to permit the socket being manually axially moved therepass and thereafter to retain the socket in the head bore until a dental tool, generally designated 50, or a manual force is used to push the socket out of the head bore. A radially outwardly opening annular groove 29 is provided in an axially intermediate portion of the socket. The groove is in part defined by annular socket surfaces 29b that are parallel to one another and perpendicular to the central axis of the socket bore.

For drivingly reciprocating the socket, there is provided an attachment drive shaft (drive member), generally designated 33, that is mounted in the housing sleeve and neck bores to have one end extend into the head bore. That is, the shaft includes an axially elongated, reduced diameter end portion 34 that is primarily located in the sleeve bore and is adapted to be drivenly rotated by the handpiece 10 in a conventional manner. The end part of the reduced diameter portion 34 remote from the handpiece is joined to one axial end of the shaft main body 35 while the opposite end of the main body is joined to the intermediate diameter portion (eccentric mount) 37. The axial opposite end of the intermediate diameter portion is joined to the eccentric pin 38 The central axes C—C of the main body, the reduced diameter portion and the intermediate portion are coextensive while the eccentric pin central axis is radially offset from the central axis of the intermediate diameter portion 37.

As shown in FIG. 1 wherein the eccentric pin is in abutting relationship to the top wall 29b of the socket groove, there is a little longitudinal play between the groove bottom wall 29b and surface of the eccentric pin that is diametrically opposite to the top wall 29b. The axial dimension of the groove throughout its circumferential dimension is substantially constant and is sufficiently small, that with the tool remaining in the same position shown, the eccentric pin can be rotated substantially less than 90 degrees about the axis C—C before it abuts against the bottom wall 29b. Thus, it is impossible for the shaft to rotate angularly through 360 degrees without having engaged both the top and bottom walls that in part define the groove 29b when the housing is retained in one fixed position.

A bushing 39 is provided on the shaft reduced diameter portion to abut against the main body, the combination of the bushing and the main body being located in the enlarged diametric bore part 20b of the bore 20 which is axially intermediate the axial opposite ends of the bore 20. The bore part 20b is in part defined by oppositely facing annular shoulders 22, 23, shoulder 23 being in the slotted collar. After the socket is inserted in the head bore, the eccentric pin is inserted into the sleeve bore and then the shaft moved transversely axially, and rotated, if necessary, so that the eccentric pin extends into the socket groove. As the shaft is moved axially in the sleeve toward the head, due to the radial inner taper of the part of the collar axially between shoulder 23 and the terminal end of the collar remote from the head in a direction axially away from the head and the slots extending through the tapered part, the main body can be moved axially into the neck. When the shoulder of the shaft at the juncture of its intermediate diameter portion with the main body abuts against the neck shoulder 22, the shaft is in the appropriate axial position relative to the housing to reciprocate the socket as the shaft is being drivenly rotated by the handpiece.

The shaft reduced diameter portion 34 is rotatably mounted by the bushing 39 while the maximum crest diameters of the grooved portions 40 of the bushing are slightly greater than the diameter of the bore 20b whereby the bushing is precluded from rotating within the bore 20b. The grooves 40 facilitate the movement of the bushing into the bore portion 20b while at the same time enhance the blocking of rotation of the bushing within the housing. The bushing extends axially between the shaft main body and the shoulder 23 to retain the shaft in an axial position relative to the housing for the eccentric 38 to reciprocate the socket.

Prior to the insertion of the socket into the head bore, a rotational restrainer 44 is mounted to the socket to be located in the socket groove 29, the axial height of the rotational restrainer being slightly less than the axial dimension of the socket groove such that there is not any significant axial play between the rotational restrainer and socket. The rotational restrainer is partially annular, the restrainer having an arcuate cutout to provide angularly spaced, axial edge surfaces 44b.

Figure 2:
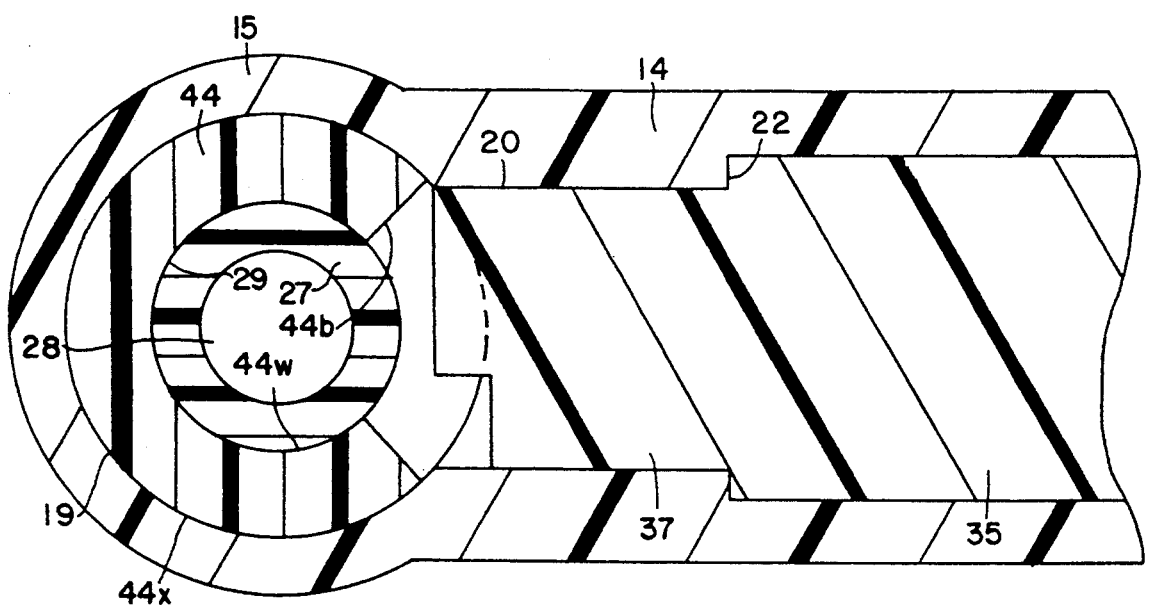
FIG. 2 is an enlarge fragmentary cross sectional view that is generally taken along the line and in the direction of the arrows 2—2 of FIG. 1, other than the shaft has been rotated 90 degrees from the showing in FIG. 1.

The diameter of the inner circumferential wall 44w of the restrainer 44 is slightly less than the minimum outer diameter part of the socket which forms the circumferential surface 29c of the groove 29 while the diameter of the outer circumferential wall 44x of the rotational restrainer is slightly greater than the diameter of the head bore below the shoulder 15b, other than for the head protrusion 30. Additionally, the maximum angular spacing (included angle) of the restrainer edges 44b is substantially less than 180 degrees, but only slightly greater than that necessary for the shaft to rotate through 360 degrees without the eccentric pin abutting against either of the edges 44b during the time the eccentric pin is abuttable against the socket edges 29b to longitudinally reciprocate the socket. Thus, the rotational restrainer has radially inner and outer circumferential surfaces 44w and 44x abutting against the circumferential wall 29c of the socket groove and the head wall defining the head bore respectively, axially opposite edge surfaces 44b with the circumferential surfaces extending therebetween and axially opposite, arcuately curved end surfaces 44c extending radially between the circumferential surfaces and arcuately between edge surfaces. The edge surfaces 44b are sufficiently angularly spaced to permit the shaft rotating through 360 degrees while the eccentric pin remains out of engagement with the edge surfaces 44b. The restrainer edge surfaces throughout their entire area may extend substantially radially relative to the central axis of the head bore as shown in FIG. 2, or each edge may initially extend radially outwardly of the head central axis and thence extend parallel to one another in a radial outward direction relative to the rotational restrainer central axis. Advantageously, the angular spacing of the edges 44b is such that the maximum rotation of the tool 50 (which will be described below) during a 360 degree rotation of the shaft, is less than about 10 to 15 degrees without the eccentric pin abutting against one or the other of the arcuate opposite edges 44b.

Prior to axially moving the drive shaft sufficiently to have the eccentric pin extend into the head bore, the socket with the rotational restrainer in the socket groove is inserted into the head bore with the restrainer cut out defined by the edges 44b facing toward bore 20. Then, the shaft is axially moved toward the head to have the eccentric pin move into the cut out, together with any necessary rotation of the shaft and/or the socket and/or rotational restrainer so that the shaft is in drivable relationship with the socket.

Figure 16:
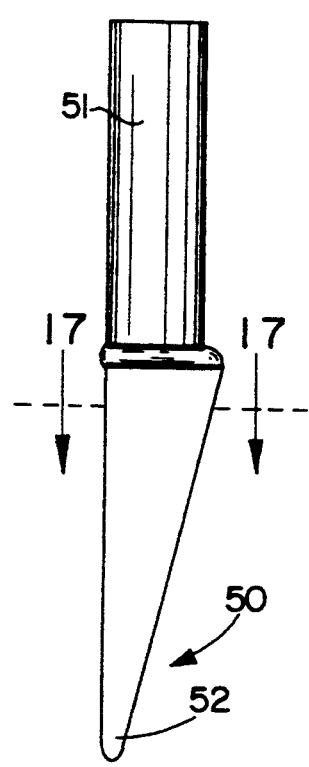
FIG. 16 is a side view of one of the tools that may be used with the attachment of this invention.
Figure 17:
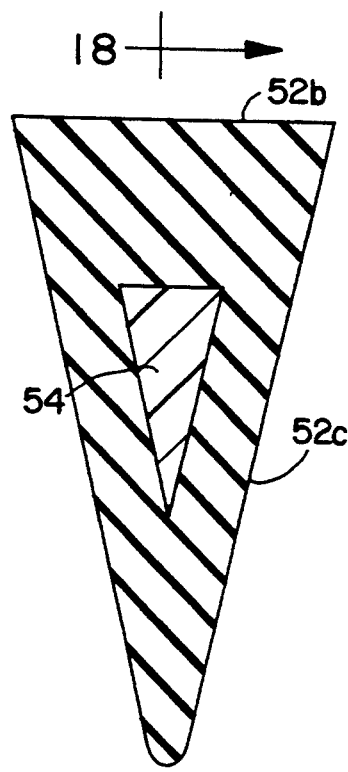
FIG. 17 is a transverse cross sectional view of a dental tool that is generally taken along the line and in the direction of the arrows 17—17 of FIG. 16.
Figure 18:
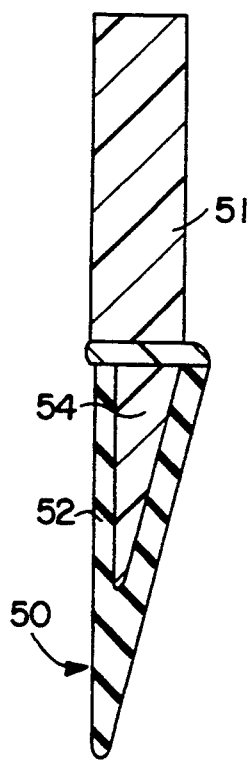
FIG. 18 is a cross sectional view that is generally taken along the line and in the direction of the arrows 18—18 of FIG. 17.

The tool or bit, generally designated 50, that is to be reciprocated by the attachment of the first embodiment may be of a construction such as indicated in FIGS. 16–18; however it may be any one of a number of conventional types. The tool has a shank 51 of an outer diameter to form a friction fit with the socket wall that defines the socket bore 28 to retain the tool in fixed relationship to the socket during normal usage, but at the same time being manually replaceable by the dentist or dental technician performing the dental procedures. The tissue or tooth engaging portion (working surface) 52 which may engage hard tissue such as a tooth 53 or soft tissue such as that of the gingiva (gum tissue) 57 (see FIG. 8), may be any one of a number of different types. For example, part 52 may be one of the different types referred to in U.S. Pat. Nos. 4,984,985 to Edwardson or 3,552,022 to Axelson and used for the types of treatments referred to therein. The tool may be made of plastic, rubber or metal and, may or may not, have an abrasive material embedded therein.

FIG. 8 diagrammatically illustrates the tool 52 engaging a tooth surface 53b adjacent the juncture of the root 53c adjacent to the crown 53d of the tooth 53 together with part of the gingiva 57 broken away to show the tooth supporting bone 58.

Each of the housing, shaft, socket and rotational restrainer of the first embodiment is made of plastic and is a one piece molded structure which is molded as a single piece, advantageously by injecting molding. That is, none of the housing, shaft, socket and rotational restrainer is made up of two or more parts that are subsequently welded or otherwise joined together.

Advantageously, prior to actuating the drive to the shaft, the dentist manually rotates the tool relative to the socket and thereby to a desired angular position relative to the attachment head and thereby relative to the rotational restrainer so that the tool working surface 52c will be at or closed to the desired relationship relative to, for example, a tooth, after the attachment head is inserted into the mouth. When the shaft is being drivenly rotated, the tool is reciprocated and the bit portion 52 is out of engagement with body tissue and other solid objects, except for the socket, the rotation restrainer prevents the socket and thereby the tool from rotating any significant angular amount relative to the head. However, upon the bit portion engaging gum or tooth tissue, the tool can rotate relative to the head upon the slightest pressure resulting from the bit portion 52 engaging a tooth or gum tissue.

Figure 9:
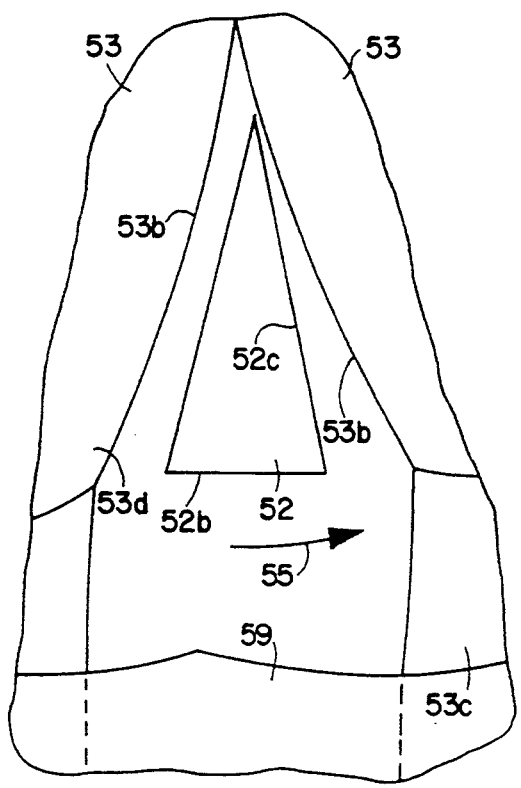
FIG. 9 is a somewhat diagrammatic indication of the rotational feature of the tool when it engages a tooth or gum tissue as the tool is being reciprocated.
Figure 10:
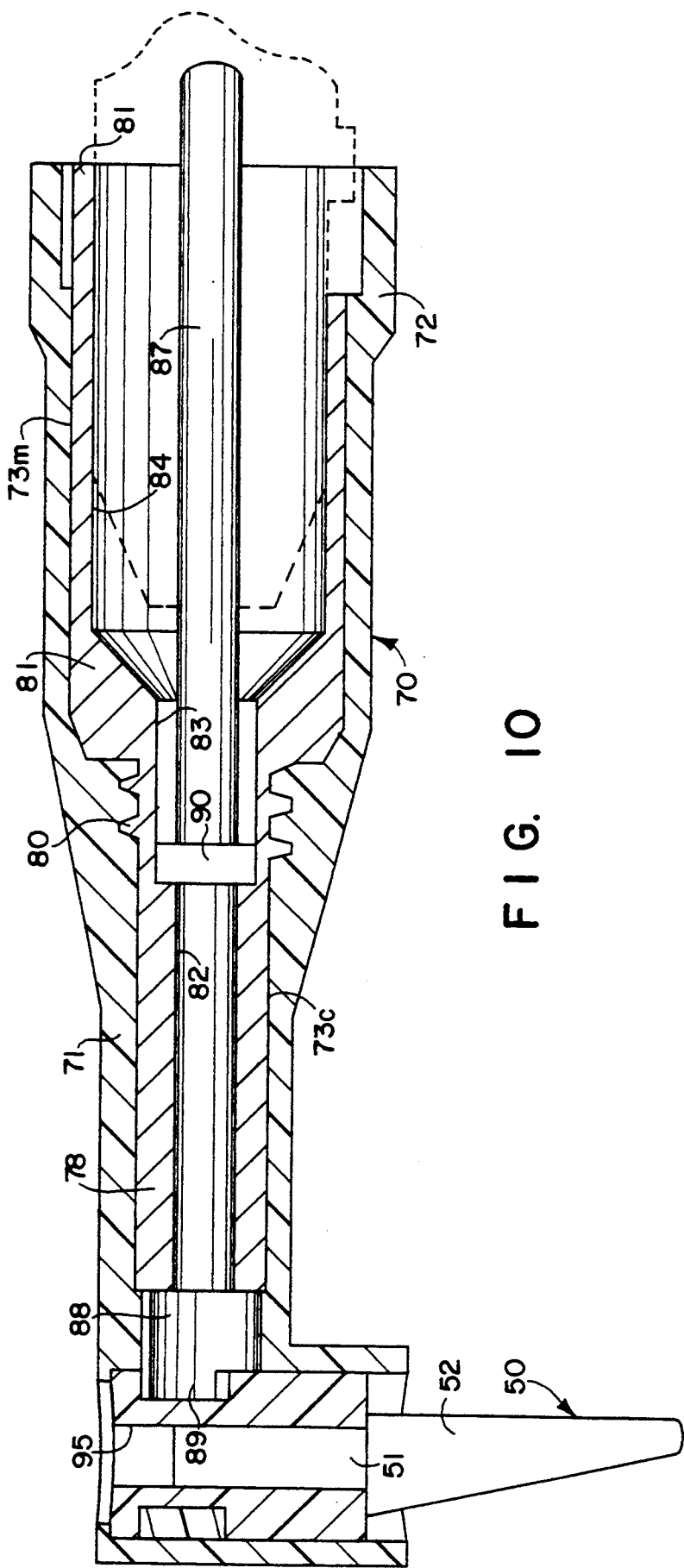
FIG. 10 is a view corresponding to FIG. 1 other than it is of the second embodiment of the invention.
Figure 14:
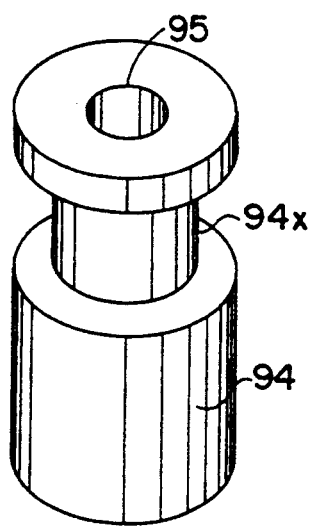
FIG. 14 is a perspective view of the socket of the second embodiment.
Figure 15:
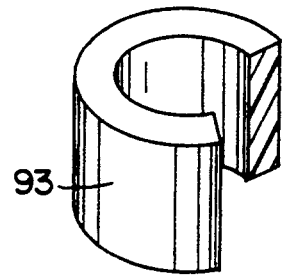
FIG. 15 is a fragmentary perspective view of the rotational restrainer of the second embodiment.

To permit rotation of the tool, the rotational socket rotates relative to the head and the rotational restrainer. Thus the degree of rotation is dependent upon the contour of the tissue engaged and the surface of the bit portion 52 For example, if the bit portion in transverse cross section is generally triangular such as shown in FIGS. 9 and 17 and has at least one, and advantageously two, nearly flat surfaces 52c that are of a substantially greater transverse dimensions than its surface 52b that extends at an angle thereto, which may be generally at a right or an acute angle to the respective working surface 52c, and the wider surfaces 52c of the bit portion 52 engages a tooth adjacent to the juncture of the bit width surfaces (opposite the narrow surface 52b), the slightest pressure resulting from the bit portion bearing against the tooth will result in the bit rotating in the direction of the arrow 55 to a position that, at least as nearly as possible taking the resiliency of the part 52 and contour of the adjacent tooth surface, a major portion of the tool working surface 52c bears against the tooth surface prior to the removal of any significant material from the tooth (normal working position such as indicated in FIGS. 8 and 20). Thus, the provision of the rotational restrainer permits self angular adjustment of the tool relative to the attachment head and thereby constitutes a safety feature minimizing possible injury to the tooth or gum tissue. This is in contrast to prior art apparatus wherein the tool is prevented from rotating relative to the attachment head and the entire handpiece has to be rotated. Further, the provision of the rotational restrainer facilitates properly aligning the tool relative to the tissue in contrast to apparatus wherein the tool is freely rotatable relative to the attachment head. For example, as indicated in FIG. 20, by manually holding the tool in a stationary position, the attachment may be rotated from the solid line position to either of the dotted line positions. In contrast to the present invention, with the tool being freely rotatable relative to the head such as occurs using some prior art devices, there is a substantially greater difficulty in at least approximately properly angularly aligning the tool working surface relative to the tooth prior to the tool initially engaging the tooth. Thus, if it were not for the self adjusting feature and the tool engaged the tooth such as shown in FIG. 2, it would tend to abrade a ridge in the tooth at the area of contact, which is undesirable. With the self adjusting feature, the use of the tool is facilitated in that the dentist or dental technician has to do less manipulating of the handpiece and is less likely to have the tool engage unintended areas of the mouth. Additionally, if the tooth engaging portion 52 is flexible such as referred to herein, the tooth engaging portion would flex to more nearly conform to the curvature of the area of the tooth at the area of contact by the surface portion 52 that is adjacent to the tooth being treated. For example, the portion 52 would flex such as indicated in FIG. 8 during normal usage.

Referring to FIG. 10-15, the second embodiment of the attachment of this invention includes an outer housing, generally designated 70. The outer housing includes a head 15 which advantageously may be the same as the head of the first embodiment, an axially elongated neck 71 having one end joined to the head and an axially elongated sleeve 72 having one end joined to the opposite end of the neck. The neck and sleeve extend transversely relative to the head. The housing has a transverse bore 73 that at one end opens to the head bore 19, which has a longitudinal central axis R—R, and at the opposite end opens through the axial opposite end of the sleeve, the transverse bore 73 having a central transverse axis T—T. That is, the combined neck and sleeve bore 73 has a reduced diameter end portion 73b opening to the head bore 19 and to the sleeve intermediate diameter bore portion 73c to form an annular shoulder 73d.

The opposite end of the bore portion 73c opens to the axially elongated, enlarged diameter bore portion 73m axially adjacent to the juncture of the neck to the sleeve. The housing has threaded grooves 73h opening to the neck bore portions axially adjacent to the opening of the neck bore portion to the sleeve bore portion 73m, the sleeve bore portion being of a larger diameter than intermediate bore portion 73c.

An inner housing, generally designated 77, includes an axially elongated, reduced diameter portion 78 located within the housing neck bore portion 73c and has one end abuttable against the shoulder 73d. The axial opposite end portion of the reduced diameter portion 78 has threads 80 formed integrally therewith to form a mating fit with grooves 73h. The opposite end of the reduced diameter portion 78 is joined to one end of the main body 81, the latter being located in the outer housing bore portion 73m.

A drive shaft 87-89 has its axially elongated reduced diameter portion 87 extending axially through bore portions 82-84 to have its one end portion adapted to be drivenly connected to the handpiece 10 in a conventional manner while its opposite end is integrally joined to a circular cylindrical eccentric mount 88. The mount is located in the outer housing bore portion 73b. The shaft also includes an eccentric pin 89 joined to the mount 88 axially opposite shaft portion 87 and radially offset therefrom. There is provided a bearing 90 on an axially intermediate part of the shaft reduced diameter portion to abut against the annular shoulder which is formed at the juncture of the inner housing intermediate and enlarged bore portions 82, 83.

A rotational restrainer 93 is mounted in the groove 94x of the socket 94 which in turn is mounted in the head bore of the second embodiment, the restrainer 93 and the socket 94 being the same and functioning in the same manner as the rotational restrainer and socket of the first embodiment. Further the socket 94, which has an axial bore 95, mounts a tool 50 in the same manner described relative to the first embodiment and is reciprocated by pin 89 extending into the socket annular groove 94x.

The attachment of the second embodiment is used in the same manner as the attachment of the first embodiment.

One example of the tool 50 which may be used with the attachment of this invention, has its tooth engaging portion 52 of of a generally pyramidal shaped and in part mounted to a generally pyramidal shaped core 54 which longitudinally extends therein in generally transversely centered relationship thereto. The base of the core may be integrally joined to one axial end of the shank 51 while at least part of the base of the tooth engaging portion 52 may be joined to the same end of the shank.

If the tooth engaging portion 52 is provided with a core 54, advantageously the tooth engaging portion has abrasive material embedded therein while the core does not. Further, in such an event, advantageously the tooth engaging portion 52 is of substantially greater flexibility than that of the core. Whether or not the tooth engaging portion 52 is of a type having a core extending therein, desirably it is of a flexibility to curve such as indicated in 8.

Each of the housing, shaft, socket and rotational restraint of the second embodiment is made of plastic and is of a one piece molded structure which is molded as a single piece. That is, none of the inner and outer housings, socket and rotational restrainer of the second embodiment is made up of two or more parts that are subsequently welded or otherwise joined together. The shaft of the second embodiment may be made of metal or plastic. With reference to each of the embodiments, plastics used for making the attachments of this invention may be the same as those used in making conventional attachments for rotating dental tools and cups, for a conventional attachment such as disclosed in U.S. Pat. No. 5,007,832 to Meller et al.

With the present invention there is no increase in the size of the head and thus does not interfere with access to all interproximal angles of the teeth.

With reference to each of the embodiments, no structure extends longitudinally outwardly of the head in a direction axially opposite the direction that the tooth engaging portion of the tool extends axially outwardly of the head. Additionally, each embodiment is self adjusting in that while the tooth engaging portion is out of contact with anything solid, with the possible exception of the socket, the tool remains in a substantially fixed angular position relative to the head, even while the tool is being reciprocated; and once the tool engages an external solid body, for example a tooth or gum, the rotational restrainer permits the socket to rotate such that the tool changes its angular position relative to the head to minimize possible injury to the gums or other parts of the mouth and removal of material from the teeth other than that desired (rotated to a position the tooth engaging surface of the tool most nearly forms a mating fit with the tooth surface as the tool is reciprocated). Thus, the rotational restrainer is of a flexibility and forms a friction fit with both the socket and head so that the tool can rotate such as indicated in the preceding sentence, but at the same time prevents any significant rotation of the tool while the tool is being reciprocated and out of engagement with any solid body other than the socket. Also, each of the attachments is relatively inexpensive to produce and the attachments are disposable so as to prevent possible spreading of infections or diseases.

Even though the sleeve of each embodiment has been shown and described as being coaxial relative to the neck, it is to be understood that the sleeve may extend at an angle other than 180 degrees (coaxially) relative to the neck together with any necessary modification of the attachment drive shaft to reciprocate the tool as described (a contra-angle attachment). Additionally, a first part of the handpiece drive that extends into the sleeve may be drivingly connected to the first part by a conventional connection to a second part to extend other than coaxially with the first part (the second part and the conventional connection not being shown).

What is claimed is:

1. A dental prophy angle attachment adapted to reciprocally mount a dental tool which has a tooth engaging surface and be driven by a handpiece for carrying out a dental operation on teeth, comprising a first housing having a head that has a first surface and a longitudinal axial bore opening through the first surface, a neck extending transversely away from the head and having a first end joined to the head and an axial opposite end and a sleeve having a first end joined to the opposite end of the neck and an axial opposite terminal end, the neck and sleeve having a transverse second bore extending axially therethrough to open though the opposite terminal end and to the head bore to extend at an angle of less than 180 degrees relative thereto, and a socket mounted in the head bore for longitudinal reciprocal and rotary movement relative to the head and being adapted for removably retaining a tool in substantially fixed angular relationship relative thereto, the socket having an axially intermediate, circumferential groove opening radially toward the second bore, a drive shaft rotatably mounted in the second bore and having a first end portion adapted for being rotatably driven by a handpiece and an axially opposite eccentric pin extending into the socket groove for reciprocating the socket as the shaft is rotated, and a rotational restrainer mounted in said groove in abutting relationship to each of the head and socket to retain the socket in fixed angular relationship relative to the head, including as the socket is reciprocated, until the tool encounters external resistance to reciprocation and thence permitting the socket rotating relative to the head until the tool is in a normal dental treating angular relationship relative to at least one of a tooth and the gum.

2. The dental prophy angle of claim 1 wherein each of the housing, the socket and rotational restrainer is a plastic one piece molded structure which is molded as a single piece.

3. The dental prophy angle of claim 1 wherein the above mentioned housing comprises an outer housing having the head, neck and sleeve, the outer housing having a transverse bore extending through the sleeve and neck to open to the head bore, and an annular inner housing in the outer housing bore, the inner and outer housings having mating threaded portions.

4. The dental prophy angle of claim 1 wherein the second bore includes a first bore portion in the neck and a second bore portion in the sleeve that is of a larger diameter than the first bore portion, the housing includes a transversely slotted collar joined to the neck axially opposite the head to extend into the sleeve and provide an annular clearance space therebetween, the first bore portion extends through the collar to open to the second bore portion, the neck and collar having axially spaced, oppositely faced annular shoulders that in part define the first bore portion, and the shaft includes a main body abuttable against the neck shoulder and a reduced diameter portion joined to the main body and extending axially within the collar and the sleeve, and a plastic bearing mounted on the shaft reduced diameter portion to extend axially between the main body and the collar shoulder and abut against the collar shoulder to have the shaft reduced diameter portion extend in rotating engagement therewith, the bearing having an axially grooved surface in abutting relationship to the collar to retain the bearing in a fixed angular relationship to the collar.

5. The dental prophy angle of claim 1 wherein the rotational restrainer has radially inner and outer circumferential longitudinal surfaces, arcuately spaced edge surfaces having the circumferential surfaces extending circumferentially therebetween and longitudinally axially opposite arcuately curved end surfaces extending radially between the circumferential surfaces and angularly between edge surfaces, the edge surfaces being sufficiently arcuately spaced to permit the shaft rotating through 360 degrees while the eccentric pin remains out of engagement with the edge surface.

6. The dental prophy angle of claim 5 wherein, as the shaft rotates through an angle of 360 degrees, the eccentric pin is rotatable through a circular path of movement of a maximum diameter greater than the maximum longitudinal axial dimension of the groove.

7. The dental prophy angle attachment of claim 5 wherein the socket has a longitudinally extending circumferential groove wall that in part defines the socket groove, and wherein in a relaxed condition external of the head and groove, the restrainer outer circumferential wall is of a slightly greater diameter than the diameter of the head bore in which the socket is reciprocated and the diameter of the socket circumferential groove wall is slightly greater than the diameter of the restrainer inner circumferential wall.

8. A dental prophy angle attachment adapted to reciprocate a dental tool and being driven by a handpiece for carrying out a dental operation on teeth as the tool tooth engaging surface engages the tooth and the tool is being reciprocated, comprising a first housing having a head that has a longitudinal first bore extending axially therethrough, a neck extending transversely away from the head and having a first end joined to the head and an axial opposite end, and a sleeve having a first end joined to the opposite end of the neck and an axial opposite terminal end, the neck and sleeve having a transverse second bore extending axially therethrough to open though the opposite terminal end and to the head bore to extend at an angle relative thereto, a drive shaft mounted in the second bore and extending into the first bore, socket means mounted in the head bore for reciprocal movement relative to the head and being reciprocated by the shaft as the shaft rotates to reciprocate a dental tool, the second bore including a first bore portion in the neck and a second bore portion in the sleeve that is of a larger diameter than the first bore portion, the housing including a collar joined to the neck axially opposite the head to extend into the sleeve and provide an annular clearance space therebetween, the first bore portion extending through the collar to open to the second bore portion, the neck and collar having axially spaced, oppositely faced annular shoulders that in part are defined by the first bore portion, and the shaft including a main body abuttable against the neck shoulder and a reduced diameter portion joined to the main body and extending axially within the collar and the sleeve, and a plastic bearing mounted on the shaft reduced diameter portion to extend axially between the main body and the collar shoulder and abut against the collar shoulder to have the shaft reduced diameter portion rotatably extend therein, the bearing having a transversely grooved surface in abutting relationship to the collar to retain the bearing in a fixed angular relationship to the collar, the collar having circumferentially spaced slots extending radially therethrough and axially through the collar shoulder to the open to the sleeve bore in an axial direction away from the head, the housing and socket means being disposable and made of plastic.

9. The dental prophy angle attachment of claim 8 wherein the shaft has an eccentric pin extending transversely into the head bore, the socket means has axial opposite ends and a circumferential groove axially intermediate its opposite ends that has the eccentric pin extending thereinto, and a rotational restrainer is mounted in the socket means groove for blocking rotation of the socket means relative to the head while the socket means is being reciprocated and no external force is applied to the tool tooth engaging surface dna permitting the socket means to rotate elative to the head when an external force is exerted on the tooth engaging surface.

10. The dental prophy angle attachment of claim 8 wherein the head bore has a longitudinal central axis, the socket means has parallel surfaces perpendicular to the central axis that in part define the socket means groove, the eccentric pin has a maximum diameter circular path of movement as the shaft is rotated, the maximum diameter being substantially less than the axial spacing of the socket means surfaces.

11. The dental prophy angle attachment of claim 10 wherein the head has a head surface defining the head bore, the socket means has a circumferential groove that is in part defined by a circumferential surface that extends axially between the socket means parallel surfaces and defines part of the socket means groove, the rotational restrainer has inner and outer circumferential surfaces that respectively frictionally engage the socket means circumferential groove surface and the head surface, 12. The dental prophy angle attachment of claim 10 wherein the rotational restrainer includes axially extending edge surfaces that are of an arcuate spacing to permit the eccentric pin rotating through 360 degrees while not being engaged by the pin and being abutted by the pin when an external force acts to rotate the tool engaging surface relative to the head as the socket means is reciprocated.

* * * * *